Figure 1:
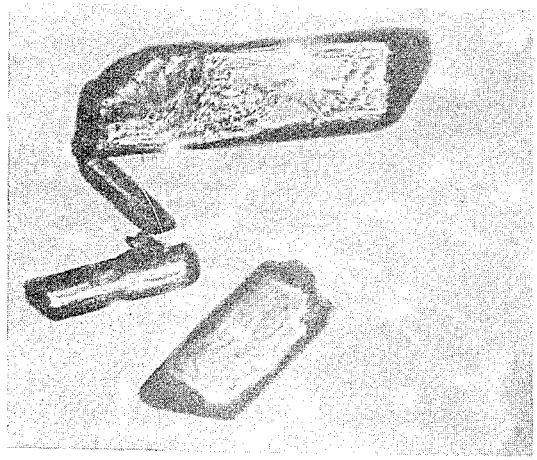

United States Patent [19]

Fujino et al.

[11] 3,959,247
[45] May 25, 1976

[54] TRH TARTRATE CRYSTALS

[75] Inventors: Masahiko Fujino, Takarazuka; Chitoshi Hatanaka, Kyoto, both of Japan

[73] Assignee: Takeda Chemical Industries, Ltd., Osaka, Japan

[22] Filed: June 21, 1974

[21] Appl. No.: 481,909

[30] Foreign Application Priority Data

July 2, 1973 Japan................................ 48-74973

[52] U.S. Cl. ........................................ 260/112.5 TR
[51] Int. Cl.² ................... C07C 103/52; C07G 7/00
[58] Field of Search ................................ 260/112.5

[56] References Cited
OTHER PUBLICATIONS

Gillessen et al., Helv. Chim. Acta, 53, 63–72, (1970).

Inouye et al., Bull. Chem. Soc. Japan, 44, 1689–1691, (1971).
Baugh et al., Endocrinol., 87, 1015–1021, (1970).
Boler et al., J. Med. Chem., 14, 475–476, (1971).
J. D. Roberts and M. C. Caserio, "Basic Principles of Organic Chemistry," Benjamin, Inc., New York, 1965, p. 598.

*Primary Examiner*—Lewis Gotts
*Assistant Examiner*—Reginald J. Suyat
*Attorney, Agent, or Firm*—Wenderoth, Lind & Ponack

[57] ABSTRACT

Crystalline thyrotropin releasing hormone (TRH) tartrate was obtained for the first time from a solution comprising TRH, tartaric acid and a certain solvent. The crystals are very pure and very stable against moisture for a long period of time.

6 Claims, 5 Drawing Figures

2θ

2θ

$2\theta$

TRH TARTRATE CRYSTALS

The present invention relates to novel crystalline L-pyroglutamyl-L-histidyl-L-proline amide (thyrotropin releasing hormone; hereafter sometimes referred to briefly as "TRH") tartrate.

While TRH has heretofore been prepared by various methods, the final products are invariably amorphous powders such as solvent-free and/or lyophilized products and no crystalline products have been available as yet. These non-crystalline or amorphous powders are generally low in purity, suffer a large variance of purity between product lots and are hygroscopic and unstable. Therefore, attempts have been made, in vain, to produce crystals in hopes of obtaining high-purity, homogeneous and non-hygroscopic products.

The principal object of the present invention is to provide novel TRH tartrate crystals which is very stable against moisture.

Another object of the present invention is to provide an industrially feasible method for producing the said TRH tartrate crystals.

The TRH tartrate crystals of the present invention can be obtained by causing TRH to separate as crystals from a solution comprising TRH, tartaric acid and a solvent to be included in the crystals as a solvent of crystallization.

TRH as it is to be employed according to this invention may be in any form, e.g. the free compound or the corresponding acetate or hydrochloride, for instance, and may be of any purity grade.

When use is made of the above-mentioned acetate or hydrochloride, for instance, it may before use be converted to the free base by means of an ion exchange resin (for example, a basic anion exchange resin, e.g. Amberlite IRA-400, Amberlite IRA-410, Amberlite IR-4B, Dowex 1, Dowex 2, Dowex 3, etc.), if so desired.

Tartaric acid can be used not only in the free form but also as salts (e.g. calcium, potassium, sodium and other salts). When TRH is used in the form of salts with acids, it is advantageous to employ tartaric acid in the above-mentioned salt form.

While the proportion of tartaric acid is not particularly critical for the purposes of this invention, it is used in amounts not less than about 0.5 mole and, preferably, from 0.8 to 1.4 moles per mole of TRH.

The solvent may be any solvent which can be included in the crystal of TRH tartrate as a solvent of crystallization, for instance, water, methanol, acetonitrile, etc.

To cause crystals of TRH tartrate to separate from a solution comprising TRH, tartaric acid and a solvent system containing a solvent to be included in the crystals as a solvent of crystallization, crystallization procedures known per se can be employed with success. For example, use can be made of the method in which a solvent miscible with said solution but does not dissolve TRH tartrate at all of appreciably, e.g. ethanol, n-propanol, isopropanol, acetone, dioxane or the like, is added to the abovementioned solution so as to depress the solubility of TRH tartrate in the mixed solvent, the method which comprises cooling a saturated solution to cause the solute to crystallize by taking advantage of the variable solubility of the solute at different temperatures of the solvent, and the method comprising removal of the solvent from said solution by distillation.

The crystals separating out from the solution can be harvested by recovery procedures known per se, examples of which are filtration and centrifugation.

The TRH tartrate crystals thus obtained by the method mentioned above are of excellent homogeneity, each crystal being formed as the molecular compound consisting of equimolar proportions of TRH and tartaric acid further includes an equimolar proportion of the solvent of crystallization.

Moreover, the solvent of crystallization in the crystal can be replaced with another solvent by contacting a TRH tartrate crystal including a certain solvent as a solvent of crystallization with another solvent. That is, a TRH tartrate crystal including water as the solvent of crystallization (hereafter referred to sometimes as TRH tartrate-water) can be converted to a TRH tartrate crystal including methanol or acetonitrile as the solvent of crystallization (hereafter referred to sometimes as TRH tartrate-methanol or TRH tartrate-acetonitrile, respectively) and the latter crystal can be dissolving Conversely, TRH tartrate-methanol or TRH tartrate-acetonitrile can be converted to a crystal of TRH tartrate including another solvent of crystallization and the latter crystal can be harvested.

For example, TRH tartrate-methanol crystals can easily be obtained by adding more than 3 times and preferably 5 to 15 times the weight of TRH tartrate-water crystals of methanol and harvesting the resultant transformed crystals by the recovery procedure set forth above. Similarly, TRH tartrate-methanol crystals can be transformed to TRH tartrate-water crystals and the latter crystals can be harvested. Thus, TRH tartrate-water crystals can be obtained by adding water to TRH tartrate-methanol crystals in a proportion corresponding to not less than 0.05 and preferably 0.1 to 5 times the weigght of said crystals and harvesting the transformed crystals according to the recovery procedure described above.

The crystals thus obtained are very pure and very stable against moisture for a long period of time. TRH tartrate or TRH tartrate-water is less-toxic to human beings or animals and is useful as medicine for the same purposes as those of TRH, for instance, anti-depressor or agent for diagnosis of hypophysis function. And, the dosage, preparation and administration means may be determined referring to those of TRH itself. Further, a pure preparation of TRH can easily be obtained by separating out TRH from a solution disslving TRH tartrate crystals by means of ion exchange resin. Therefore the crystallization of TRH tartrate can advantageously be applied to purification of TRH.

FIG. 1 of the accompanying drawing shows a photograph of TRH tartrate-water crystals of the present invention magnified 124 diameter with a microscope.

Figure 2:
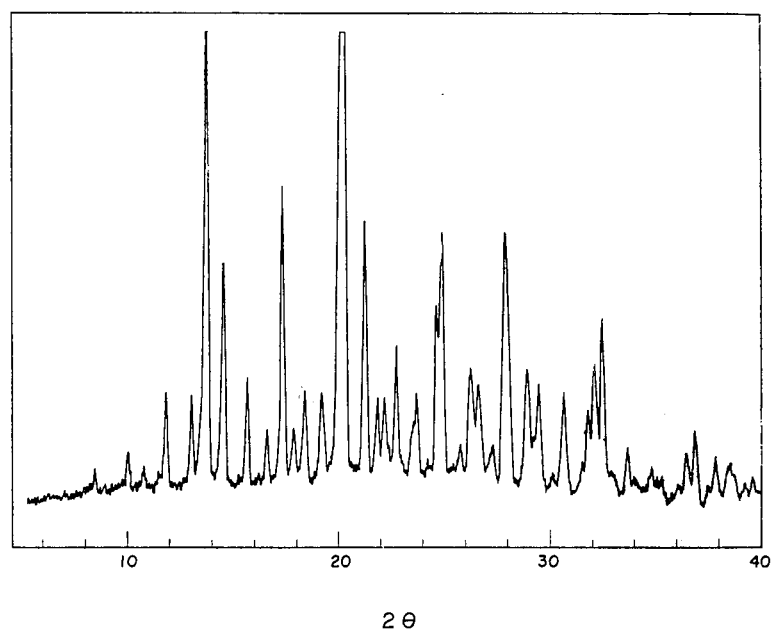

FIG. 2 of the accompanying drawing shows a X-ray diffraction pattern of TRH tartrate-water measured by the powder method, and the significant lattice spacings are as follows:

| | | |
|---|---|---|
| 2.74 | angstrom | (middle) |
| 3.18 | angstrom | (middle) |
| 3.39 | angstrom | (weak) |
| 3.56 | angstrom | (middle) |
| 3.60 | angstrom | (middle) |
| 3.87 | angstrom | (middle) |
| 4.17 | angstrom | (middle) |
| 4.37 | angstrom | (strong) |
| 5.09 | angstrom | (middle) |
| 5.63 | angstrom | (middle) |
| 6.06 | angstrom | (middle) |
| 6.41 | angstrom | (strong) |

-continued

| | | |
|---|---|---|
| 7.43 | angstrom | (weak) |

Further, nuclear magnetic resonance spectrum of the TRH tartrate-water crystals is measured, and the significant δ values are as follows:

($D_2O$) δ : 8.70(s, 1, Im-2H-His), 7.43(s, 1, Im-4H-His), 5.10 (T, 1, αH-His), 4.60(s, 2, α-and β—CH—tart), 4.54–4.34 (m, 2, αH-Pro and αH-pGlu), 3.82–3.62(m, 2, δδ'—$CH_2$—Pro), 3,32(q, 2, ββ'—$CH_2$—His), 2.60–1.92(m, 8, ββ'+δδ'—$CH_2$—pGlu and ββ'+δδ'—$CH_2$—Pro).

Figure 3:
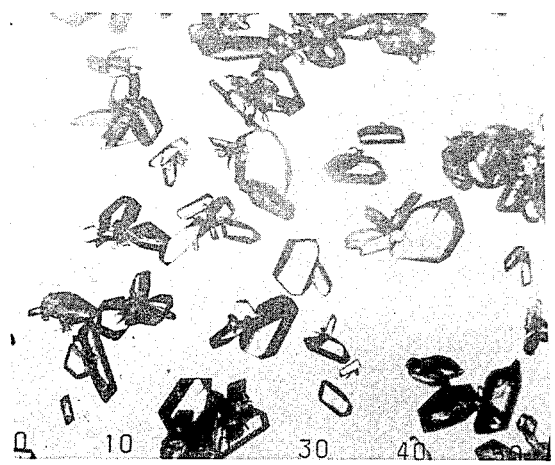

FIG. 3 of the accompanying drawing shows a photograph of TRH tartrate-methanol crystals of the present invention magnified 100 diameter with a microscope.

Figure 4:
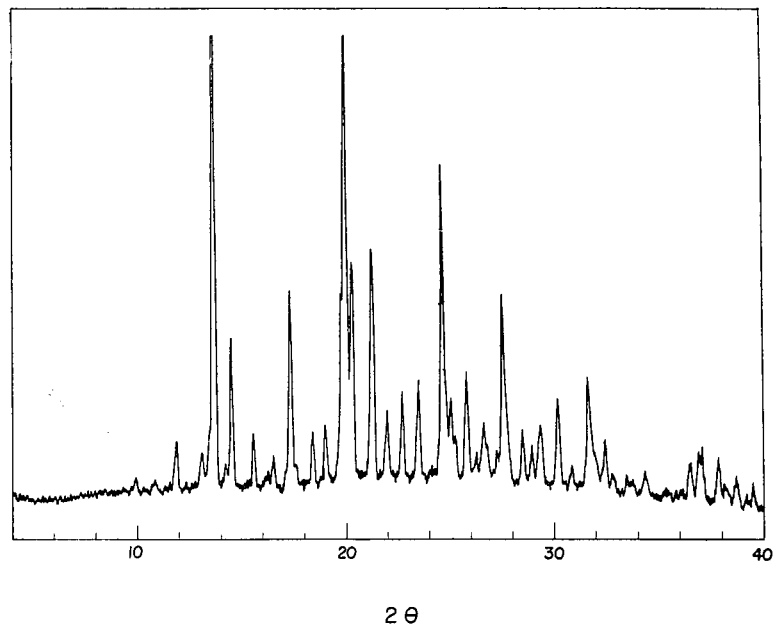

FIG. 4 of the accompanying drawing shows an X-ray diffraction pattern of TRH tartrate-methanol measured by the powder method, and the significant lattice spacings are as follows:

| | | |
|---|---|---|
| 2.82 | angstrom | (weak) |
| 2.96 | angstrom | (weak) |
| 3.45 | angstrom | (middle) |
| 3.60 | angstrom | (middle) |
| 3.79 | angstrom | (weak) |
| 3.90 | angstrom | (weak) |
| 4.17 | angstrom | (middle) |
| 4.35 | angstrom | (middle) |
| 4.42 | angstrom | (strong) |
| 4.48 | angstrom | (middle) |
| 5.10 | angstrom | (middle) |
| 6.07 | angstrom | (middle) |
| 6.42 | angstrom | (strong) |

Further, nuclear magnetic resonance spectrum of the TRH tartrate-methanol crystals is measured, and the significant δ values are as follows:

($D_2O$) δ : 8.70(s, 1, Im-2H-His), 7.43(s, 1, Im-4H-His), 5.10 (T, 1, αH-His), 4.60(s, 2, α-and β—CH—tart), 4.54–4.34 (m, 2, αH-Pro and αH-pGlu), 3.82–3.62(m, 2, δδ'—$CH_2$—Pro), 3.4(s, 3, $CH_3OH$), 3.32(q, 2, ββ'—$CH_2$—His), 2.60–1.92 (m, 8, ββ'+δδλ'—$CH_2$—pGlu and ββ'+δδ'—$CH_2$—Pro).

Figure 5:
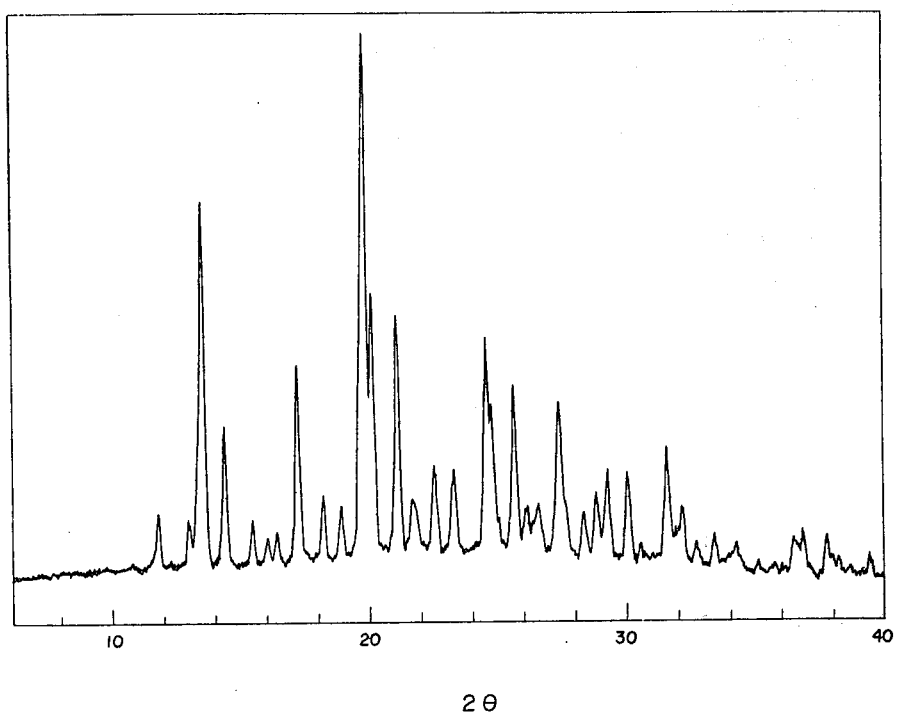

FIG. 5 of the accompanying drawing shows an X-ray diffraction pattern of TRH tartrate-acetonitrile measured by the powder method, and the significant lattice spacings are as follows:

| | | |
|---|---|---|
| 2.83 | angstrom | (weak) |
| 3.04 | angstrom | (weak) |
| 3.24 | angstrom | (middle) |
| 3.47 | angstrom | (middle) |
| 3.59 | angstrom | (middle) |
| 3.62 | angstrom | (middle) |
| 3.93 | angstrom | (weak) |
| 4.19 | angstrom | (middle) |
| 4.40 | angstrom | (middle) |
| 4.46 | angstrom | (strong) |
| 5.13 | angstrom | (middle) |
| 6.11 | angstrom | (weak) |
| 6.51 | angstrom | (middle) |

Further, nuclear magnetic resonance spectrum of the TRH tartrate-acetonitrile crystals is measured, and the significant δ values are as follows:

($D_2O$) δ : 8.70(s, 1, Im-2H-His), 7.43(s, 1, Im-4H-His), 5.10 (T, 1, αH-His), 4.60(s, 2, α-and β—CH—tart), 4.54–4.34(m,2, αH-Pro and αH-pGlu), 3.82– 3.62(m, 2, δδ'—$CH_2$—Pro), 3.32(q, 2, ββ'—$CH_2$—His), 2.60–1.92(m, 8 , ββ'+δδ'—$CH_2$—pGlu and ββ'+δδ'-$CH_2$-Pro), 2.1(s, 3, $CH_3CN$).

For further explanation of the present invention, following examples are given wherein the word "part(s)" is based on weight unless otherwise noted, and relation between "part" and "volume part" corresponds to that between gram and milliliter.

EXAMPLE 1

In 50 volume parts of water are dissolved 19 parts of TRH monohydrate and 7.5 parts of L-tartaric acid, and while the solution is warmed to 70°C, ethanol is added in installments. Immediately after a slight turbidity is observed, the temperature is gradually brought down to room temperature, at which temperature the solution is allowed to stand for 3 days. Then, the solution is cooled to 10°C and allowed to stand for 2 days to allow crystallization to be completed. The crystals thus obtained are harvested by filtration, washed with hot ethanol and dried under reduced pressure at 50°C for 1 hour and at 80°C for 5 hours. The described procedure yields 18 parts of TRH tartrate-water as crystals melting at 127°C–130°C. $[α]_D^{24}$ =–49.90°($c$=1.05 in water)

Elemental analysis, for $C_{16}H_{22}O_4N_6 \cdot C_4H_6O_6 \cdot H_2O$; Calcd.: C, 45.28; H, 5.70; N, 15.84; Found: C, 45.21; H, 5.70; N, 15.81.

Crystals of TRH tartrate-water obtained above are dried under reduced pressure (0.5 mmHg) at 80°–90°C for 8 hours, whereby crystals of TRH tartrate-water melting at 150-155°C (with decomposition) are obtained.

Elemental analysis, for $C_{16}H_{22}O_4N_6 \cdot C_4H_6O_6 \cdot ½H_2O$; Calcd.: C, 46.06; H, 5.60; N, 14.46; Found: C, 45.97; H, 5.63; N, 14.33.

EXAMPLE 2

In 30 volume parts of water are dissolved, under heating, 3.8 parts of powdery TRH and 1.5 part of L-tartaric acid. After the solution has been cooled to room temperature, a few pieces of crystal obtained according to Example 1 are added as seeds and the water is evaporated off gently in a desiccator, whereupon the entire residue is obtained as crystals.

Following the addition of a relatively small amount of cold ethanol, the crystals are harvested by filtration, washed with ethanol and dried. The described procedure yields 4.6 parts of TRH tartrate-water as crystals melting at 127°C–130°C. $[α]_D^{24}$ =–49.90° ($c$=1.05 in water)

EXAMPLE 3

In 25 volume parts of methanol are dissolved, under heating 1.9 part of crude TRH (including approximately 10 % of impurity) and 0.75 part of L-tartaric acid, and the solution is allowed to stand at room temperature for 7 days. The resultant crystals are harvested by filtration and dried under reduced pressure at 50°C for 5 hours. The described procedure yields 1.8 part crystals of a molecular compound of TRH tartrate including one molecule of methanol as crystals melting at 137°C–140°C $[α]_D^{24}$ =–46.90° ($c$=1.01 in water)

Elemental analysis, for $C_{16}H_{22}O_4N_6 \cdot C_4H_6D_6 \cdot CH_3OH$; Calcd.: C, 46.32; H, 5.92; N, 15.44; Found: C, 46.19; H, 5.91; N, 15.29.

EXAMPLE 4

In 60 volume parts of methanol are dissolved, under heating 3.6 parts of dry TRH powder and 1.5 part of L-tartaric acid.

A total of 40 volume parts of acetonitrile is added in small portions to the above solution and the mixture is allowed to stand at room temperature for 3 days and, then, in a refrigerator for 2 days. The resultant crystals are harvested by filtration and dried under reduced pressure at 50°C for 8 hours. The described procedure yields 3.8 parts TRH tartrate-methanol as crystals melting at 137°C–140°C $[\alpha]_D^{24}=-50.25°$ ($c=1.015$ in water)

Elemental analysis, for $C_{16}H_{22}O_4N_6 \cdot C_4H_6O_6 \cdot CH_3OH$; Calcd.: C, 46.32; H, 5.92; N, 15.44; Found: C, 46.21; H, 5.90; N, 15.31.

EXAMPLE 5

In 50 volume parts of water are dissolved 19.0 parts of $TRH \cdot H_2O$ and 7.5 parts of L-tartaric acid, followed by the addition of 700 volume parts of acetone. The resultant oil is rubbed with a glass rod and the crystals formed are recovered by filtration, washed with hot ethanol and dried under reduced pressure. The described procedure yields 24.5 parts of TRH tartrate-water as crystals melting at 127°C–129°C. $[\alpha]_D^{25}=-49.45°$ ($c=1.0$ in water)

Elemental analysis, for $C_{16}H_{22}O_4N_6 \cdot C_4H_6O_6 \cdot H_2O$; Calcd.: C, 45.29; H, 5.70; N, 15.84; Found: C, 45.04; H, 5.56; N, 15.88.

EXAMPLE 6

In 25 volume parts of water are dissolved 19.0 parts of $TRH \cdot H_2O$ and 7.5 parts of L-tartaric acid. To the solution is added 400 volume parts of dioxane and the resultant oil is crystallized by rubbing with a glass rod.

The crystals are recovered by filtration, washed with hot ethanol and dried under reduced pressure. The described procedure yields 22.4 parts of TRH tartrate-water as crystals melting at 126°C–128°C. $[\alpha]_D^{25}=-48.90°$ ($C=1.0$ in water)

Elemental analysis, for $C_{16}H_{22}O_4N_6 \cdot C_4H_6O_6 \cdot H_2O$; Calcd.: C, 45.28; H, 5.70; N, 15.84; Found: C, 45.00; H, 5.82; N, 15.62.

EXAMPLE 7

In 6 volume parts of 1.7 N hydrochloric acid are dissolved 3.99 parts of TRH hydrochloride and 2.62 parts pf calcium L-tartrate tetrahydrate ($CaC_4H_4O_6 \cdot 4-H_2O$), followed by the addition of 20 volume parts of ethanol. This solution is seeded with TRH tartrate-water crystals and a further amount of ethanol is added gradually to make a total of 40 volume parts added ethanol. The resultant crystals are recovered by filtration and treated in the same manner as Example 1. The described procedure yields 3.81 parts of TRH tartrate-water as crystals melting at 127°C–130°C. $[\alpha]_D^{24}=-49.90°$ ($c=1.05$ in water)

EXAMPLE 8

In 80 volume parts of acetic acid are dissolved 19 parts of TRH monohydrate and 7.5 parts of L-tartaric acid, and while the solution is warmed to 50°C, 240 volume parts of acetonitrile is added in installments. The temperature is gradually brought down to room temperature, at which temperature the solution is allowed to stand overnight. The resultant crystals are harvested by filtration, washed with acetonitrile and dried under reduced pressure. The procedure yields 25.7 parts of TRH tartrate-acetonitrile as crystals melting at 145°C–148°C. $[\alpha]_D^{22}=-47.1°$ ($c=1.0$ in water)

Elemental analysis, for $C_{16}H_{22}O_4N_6 \cdot C_4H_6O_6 \cdot CH_3CN$; Calcd.: C, 47.74; H, 5.65; N, 17.72; Found: C, 47.79; H, 5.77; N, 17.58.

What is claimed is:

1. L-pyroglutamyl-L-histidyl-L-proline amide tartrate.
2. A crystal of L-pyroglutamyl-L-histidyl-L-proline amide tartrate including a solvent of crystallization.
3. A crystal as in claim 2, wherein the solvent of crystallization is a member selected from the group consisting of water, methanol and acetonitrile.
4. A crystal as in claim 2, wherein the solvent of crystallization is water.
5. A crystal as in claim 2, wherein the solvent of crystallization is methanol.
6. A crystal as in claim 2, wherein the solvent of crystallization is acetonitrile.

* * * * *